US007829591B2

(12) United States Patent
Kumazawa et al.

(10) Patent No.: US 7,829,591 B2
(45) Date of Patent: Nov. 9, 2010

(54) FLAVANONE COMPOUND AND USES THEREOF

(75) Inventors: Shigenori Kumazawa, Shizuoka (JP); Tsutomu Nakayama, Shizuoka (JP); Kayoko Shimoi, Shizuoka (JP); Takaki Goto, Ichinomiya (JP); Syuichi Fukumoto, Aichi (JP); Tsutomu Arakaki, Naha (JP)

(73) Assignee: Pokka Corporation, Aichi (JP)

( * ) Notice: Subject to any disclaimer, the term of this patent is extended or adjusted under 35 U.S.C. 154(b) by 884 days.

(21) Appl. No.: 11/686,038

(22) Filed: Mar. 14, 2007

(65) Prior Publication Data

US 2007/0161579 A1 Jul. 12, 2007

Related U.S. Application Data

(62) Division of application No. 10/562,019, filed as application No. PCT/JP2004/008964 on Jun. 18, 2004, now Pat. No. 7,256,214.

(30) Foreign Application Priority Data

| Jun. 20, 2003 | (JP) | ............................ 2003-177332 |
| Jun. 20, 2003 | (JP) | ............................ 2003-177333 |
| Apr. 19, 2004 | (JP) | ............................ 2004-123479 |
| Apr. 19, 2004 | (JP) | ............................ 2004-123480 |

(51) Int. Cl.
*A61K 31/353* (2006.01)
*C07D 311/74* (2006.01)
(52) U.S. Cl. ..................................... 514/456; 549/403
(58) Field of Classification Search ................ 516/456; 549/403
See application file for complete search history.

(56) References Cited

U.S. PATENT DOCUMENTS

| 4,885,298 A | 12/1989 | Rimbault |
| 2001/0031735 A1 | 10/2001 | Perrier et al. |

FOREIGN PATENT DOCUMENTS

| JP | 2003061593 A | 3/2003 |

OTHER PUBLICATIONS

Chen et al, Biochemical Pharmacology, vol. 67, p. 53-66 (Jan. 1, 2004).*
Tseng et al.; "Allelopathic Potential of *Macaranga tanarius* (L.) Muell. -ARG.", Journal of Chemical Ecology, vol. 29, No. 5, pp. 1269-1286 (May 2003).
Chen et al.; "Cytotoxic Prenylflavanones From Taiwanese Propolis"; Journal of Natural Products, vol. 66, No. 4, pp. 503-506 (2003).
Bankova, VS et al. A study on Flavonoids of Propolis. J of Natural Products. 1983. vol. 46. No. 4. pp. 471-474. XP002524984.
Siess, MH et al. Flavonoids of Honey and Propolis: Characterization and Effects on Hepatic Drug-Metabolizing Enzymes and Benzo[a]pyrene-DNA Binding in Rats. J Agric Food Chem. 1996. vol. 44. No. 8. pp. 2297-2301. XP002524985.
Marcucci, MC. Propolis:chemical composition, biological properties and therapeutic activity. Apidologie. 1995. vol. 26. pp. 83-99. XP002524986.
Fujimoto, Takunori et al., Diversity of Propolis, Part 2, Propolis from Japan, Honeybee Science, 2001, 22, No. 2, pp. 67-74.
Phillips, William R. et al., C-Geranyl Compounds from *Mimulus clevelandii*, J. Nat. Prod., 1996, vol. 59, pp. 495 to 497.
Yakushijin, Kenichi et al., New Prenylflavanones From *Hernandia nymphaefolia* (PRESL) Kubitzki, Heterocycles, 1980, vol. 14, No. 4, pp. 397 to 402.
Burdock, G.A., Review of the Biological Properties and Toxicity of Bee Propolis (Propolis), Food and Chemical Toxicology, 1998, vol. 36, pp. 347 to 363.
Masuda, Toshiya et al., Flow Cytometric Estimation on Cytotoxic Activity of Leaf Extracts from Seashore Plants in Subtropical Japan: Isolation, Quantification and Cytotoxic Action of (-)-Deoxypodophyllotoxin, Phytotherapy Research, 2002, vol. 16, pp. 353-358.
Tseng, Mei-Huims et al., Allelopathic Prenylflavanones from the Fallen Leaves of *Macaranga tanarius*, J. Nat. Prod. 2001, vol. 64, pp. 827-828.
Wang, Y. Use of propolis in cosmetic and protection products. Journal of bee. 1988(5). p. 27. Kunmin, Yunnan Province, China. ISSN: 1003-9139.
Du, W. Rare Natural Health Products-Propolis. Autumn Science. 1999(7). p. 29. Haldan District, Beijing, China. ISSN: 1006-6284.

(Continued)

*Primary Examiner*—Bernard Dentz
(74) *Attorney, Agent, or Firm*—Marsh Fischmann & Breyfogle LLP

(57) ABSTRACT

Each of an antioxidant, an antimicrobial agent, an antitumor agent, a food and beverage product, cosmetics, a quasi-drug and a pharmaceutical of the present invention contains a new flavanone compound represented by the following structural formula:

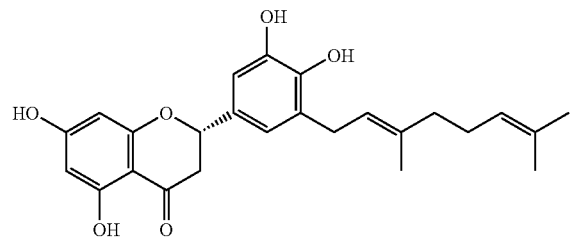

Alternatively, each of an antioxidant, an antimicrobial agent, an antitumor agent, a food and beverage product, cosmetics, a quasi-drug and a pharmaceutical of the present invention contains at least one flavanone compound selected from the group consisting of nymphaeol-A, nymphaeol-B, and nymphaeol-C.

9 Claims, 8 Drawing Sheets

OTHER PUBLICATIONS

Lee et al. Aromatase Inhibitors From *Broussonetia papyrifera*. Journal of Natural Products. 2001. vol. 64. No. 10. pp. 1286-1293. XP-001134953.

Prytzyk et al. Flavonoids and trypanocidal activity of Bulgarian propolis. Medicinal & Aromatic Plants Abstracts, Scientific Publishers, New Delhi-India. XP-018000321. (2003).

Meresta et al. Antibacterial activity of flavonoid compounds of propolis, orrurring in flora in Poland. Chemical Abstracts. 109: 35198s. XP-002130343, (1985).

Du, W. Rare Natural Health Products-Propolis. Autumn Science. 1999(7). p. 29. Haldian District, Beijing, China. ISSN: 1006-6284.

* cited by examiner

Fig. 1

Compound 1 – Physicochemical Properties

| | |
|---|---|
| Appearance | white powder |
| Molecular formula | $C_{25}H_{28}O_6$ |
| ESI-MS (m/z) | |
| Positive: | 425.3 $(M+H)^+$ |
| Negative: | 423.5 $(M-H)^-$ |
| UV $\lambda_{max}^{MeOH}$ nm ($\varepsilon$) | 288.5 (19,674) |
| IR (KBr) $cm^{-1}$ | 3420, 2960, 2920, 1680, 1600, 1160 |
| $[\alpha]_D^{24}$ (c 0.2, MeOH) | −5.8° |
| $[\alpha]_D^{25}$ (c 0.2, $CHCl_3$) | +20.0° |
| MP | 80∼83°C |
| CD (MeOH) $\theta$ /deg | 8470 (330), −46997 (290), 12833 (255) |

Fig. 2

NMR Data (Compound 1 in Acetone-$d_6$)

| Position | $^{13}$C | | $^1$H | |
|---|---|---|---|---|
| 2 | 77.21 | CH | 5.62 | (1H, dd), $J$=2.9, 11.8 Hz |
| 3 | 43.26 | CH$_2$ | 2.66 | (1H, dd), $J$=2.9, 17.2 Hz |
|   |       |        | 3.17 | (1H, dd), $J$=11.8, 17.2 Hz |
| 4 | 197.59 | C | — | |
| 5 | 165.29 | C | 12.19 | (-OH, s) |
| 6 | 95.83 | CH | 5.96 | (1H, s) |
| 7 | 167.27 | C | — | |
| 8 | 96.79 | CH | 5.96 | (1H, s) |
| 9 | 164.65 | C | — | |
| 10 | 103.12 | C | — | |
| 1' | 129.77 | C | — | |
| 2' | 127.71 | C | — | |
| 3' | 144.08 | C | — | |
| 4' | 145.56 | C | — | |
| 5' | 113.49 | CH | 6.82 | (1H, d), $J$=8.3 Hz |
| 6' | 118.55 | CH | 6.96 | (1H, d), $J$=8.3 Hz |
| 1'' | 25.15 | CH$_2$ | 3.55 | (2H, d), $J$=6.3 Hz |
| 2'' | 124.15 | CH | 5.18 | (1H, t), $J$=6.3 Hz |
| 3'' | 135.33 | C | — | |
| 4'' | 16.34 | CH$_3$ | 1.68 | (3H, s) |
| 5'' | 40.37 | CH$_2$ | 1.97 | (2H, t), $J$=6.2 Hz |
| 6'' | 27.34 | CH$_2$ | 2.05 | (2H, m) |
| 7'' | 125.02 | CH | 5.06 | (1H, dt), $J$=1.9, 6.2 Hz |
| 8'' | 131.74 | C | — | |
| 9'' | 25.75 | CH$_3$ | 1.60 | (3H, s) |
| 10'' | 17.68 | CH$_3$ | 1.55 | (3H, s) |

Fig. 3

Compound 2 – Physicochemical Properties

| | |
|---|---|
| Appearance | yellow powder |
| Molecular formula | $C_{25}H_{28}O_6$ |
| ESI-MS (m/z) | |
| Positive: | 425.0 $(M+H)^+$ |
| Negative: | 423.3 $(M-H)^-$ |
| HRFAB-MS (m/z) | |
| calcd.: | 425.1965 $(M+H)^+$ |
| found: | 425.1968 $(M+H)^+$ |
| UV $\lambda_{max}^{MeOH}$ nm ($\varepsilon$) | 288.0 (17,935) |
| IR (KBr) $cm^{-1}$ | 3360, 2960, 2920, 1680, 1600 |
| $[\alpha]_D^{25}$ (c 0.2, MeOH) | $-17.8°$ |
| MP | 123~126°C |
| CD (MeOH) $\theta$ /deg | 11444 (332), -30028 (292), 7139 (254) |

Fig. 4

NMR Data (Compound 2 in Acetone-$d_6$)

| Position | $^{13}C$ | | $^1H$ | |
|---|---|---|---|---|
| 2 | 80.13 | CH | 5.35 | (1H, dd), $J$=2.9, 12.2 Hz |
| 3 | 43.54 | CH$_2$ | 2.74 | (1H, dd), $J$=2.9, 17.1 Hz |
| | | | 3.12 | (1H, dd), $J$=12.2, 17.1 Hz |
| 4 | 197.19 | C | — | |
| 5 | 165.24 | C | 12.17 | (-OH, s) |
| 6 | 95.81 | CH | 5.95 | (1H, s) |
| 7 | 167.28 | C | — | |
| 8 | 96.74 | CH | 5.95 | (1H, s) |
| 9 | 164.31 | C | — | |
| 10 | 103.22 | C | — | |
| 1' | 130.58 | C | — | |
| 2' | 112.07 | CH | 6.91 | (1H, d), $J$=2.2 Hz |
| 3' | 145.26 | C | — | |
| 4' | 144.30 | C | — | |
| 5' | 129.02 | C | — | |
| 6' | 119.97 | CH | 6.81 | (1H, d), $J$=2.2 Hz |
| 1" | 28.83 | CH$_2$ | 3.38 | (2H, d), $J$=7.3 Hz |
| 2" | 123.36 | CH | 5.38 | (1H, m) |
| 3" | 136.39 | C | — | |
| 4" | 16.21 | CH$_3$ | 1.73 | (3H, s) |
| 5" | 40.45 | CH$_2$ | 2.06 | (2H, t), $J$=7.5 Hz |
| 6" | 27.37 | CH$_2$ | 2.12 | (2H, td), $J$=6.8, 7.5 Hz |
| 7" | 125.07 | CH | 5.12 | (1H, tq), $J$=1.5, 6.8 Hz |
| 8" | 131.70 | C | — | |
| 9" | 25.80 | CH$_3$ | 1.63 | (3H, s) |
| 10" | 17.71 | CH$_3$ | 1.57 | (3H, s) |

Fig. 5

Compound 3 – Physicochemical Properties

| | |
|---|---|
| Appearance | yellow powder |
| Molecular formula | $C_{25}H_{28}O_6$ |
| ESI-MS (m/z) | |
|     Positive: | 425.1 $(M+H)^+$ |
|     Negative: | 423.2 $(M-H)^-$ |
| UV $\lambda_{max}^{MeOH}$ nm ($\varepsilon$) | 291.5 (16,833) |
| IR (KBr) cm$^{-1}$ | 3380, 2960, 2920, 1680, 1600, 1450 |
| $[\alpha]_D^{23}$ (c 0.77, MeOH) | $-3.94°$ |
| $[\alpha]_D^{25}$ (c 0.2, CHCl$_3$) | $-6.5°$ |
| MP | 172~175°C |
| CD (MeOH) $\theta$ /deg | 9773 (335), −26940 (293), 3399 (255) |

Fig. 6

NMR Data (Compound 3 in Acetone-$d_6$)

| Position | $^{13}$C | | $^1$H | |
|---|---|---|---|---|
| 2 | 79.85 | CH | 5.35 | (1H, dd), $J$=3.0, 12.7 Hz |
| 3 | 43.64 | CH$_2$ | 2.71 | (1H, dd), $J$=3.0, 17.1 Hz |
|   |       |         | 3.12 | (1H, dd), $J$=12.7, 17.1 Hz |
| 4 | 197.26 | C | | |
| 5 | 162.24 | C | 12.46 | (-OH, s) |
| 6 | 108.99 | C | | |
| 7 | 164.76 | C | | |
| 8 | 95.27 | CH | 6.03 | (1H, s) |
| 9 | 161.91 | C | | |
| 10 | 103.09 | C | | |
| 1' | 131.69 | C | | |
| 2' | 114.67 | CH | 7.03 | (1H, s) |
| 3' | 145.95 | C | | |
| 4' | 146.28 | C | | |
| 5' | 115.97 | CH | 6.86 | (1H, s) |
| 6' | 119.18 | CH | 6.86 | (1H, s) |
| 1" | 21.53 | CH$_2$ | 3.26 | (2H, d), $J$=7.3 Hz |
| 2" | 123.44 | CH | 5.26 | (1H, td), $J$=1.0, 7.3 Hz |
| 3" | 134.96 | C | | |
| 4" | 16.18 | CH$_3$ | 1.76 | (3H, s) |
| 5" | 40.46 | CH$_2$ | 1.95 | (2H, t), $J$=7.5 Hz |
| 6" | 27.38 | CH$_2$ | 2.05 | (2H, m) |
| 7" | 125.12 | CH | 5.08 | (1H, tt), $J$=1.0, 5.4 Hz |
| 8" | 131.54 | C | | |
| 9" | 25.77 | CH$_3$ | 1.62 | (3H, s) |
| 10" | 17.66 | CH$_3$ | 1.56 | (3H, s) |

Fig. 7

Compound 4 – Physicochemical Properties

| | |
|---|---|
| Appearance | light brown gum |
| Molecular formula | $C_{30}H_{36}O_6$ |
| FAB-MS (m/z) | |
| Positive: | 493.3 $(M+H)^+$ |
| UV $\lambda_{max}^{MeOH}$ nm ($\varepsilon$) | 292.0 (20,418) |
| IR (KBr) $cm^{-1}$ | 3400, 2960, 2920, 1640, 1600 |
| $[\alpha]_D^{24}$ (c 0.2, MeOH) | +1.8° |
| $[\alpha]_D^{25}$ (c 0.2, $CHCl_3$) | +26.5° |
| CD (MeOH) $\theta$ /deg | 8810 (335), −30708 (293), 10510 (257) |

Fig. 8

NMR Data (Compound 4 in Acetone-$d_6$)

| Position | $^{13}C$ | | $^1H$ | |
|---|---|---|---|---|
| 2 | 77.12 | CH | 5.59 | (1H, dd), $J$=2.7, 13.5 Hz |
| 3 | 43.49 | $CH_2$ | 2.65 | (1H, dd), $J$=2.7, 17.2 Hz |
|   |       |        | 3.14 | (1H, dd), $J$=13.5, 17.2 Hz |
| 4 | 197.65 | C | | |
| 5 | 162.27 | C | 12.47 | (-OH, s) |
| 6 | 108.96 | C | | |
| 7 | 164.74 | C | | |
| 8 | 95.29 | CH | 6.04 | (1H, s) |
| 9 | 162.27 | C | | |
| 10 | 103.01 | C | | |
| 1' | 129.96 | C | | |
| 2' | 127.59 | C | | |
| 3' | 144.04 | C | | |
| 4' | 145.49 | C | | |
| 5' | 113.50 | CH | 6.82 | (1H, d), $J$=8.3 Hz |
| 6' | 118.51 | CH | 6.96 | (1H, d), $J$=8.3 Hz |
| 1" | 25.13 | $CH_2$ | 3.54 | (2H, d), $J$=6.5 Hz |
| 2" | 124.15 | CH | 5.18 | (1H, t), $J$=6.5 Hz |
| 3" | 135.34 | C | | |
| 4" | 16.37 | $CH_3$ | 1.64 | (3H, s) |
| 5" | 40.36 | $CH_2$ | 1.97 | (2H, t), $J$=7.0 Hz |
| 6" | 27.35 | $CH_2$ | 2.04 | (2H, m) |
| 7" | 125.02 | CH | 5.06 | (1H, qt), $J$=1.2, 7.0 Hz |
| 8" | 131.72 | C | | |
| 9" | 25.84 | $CH_3$ | 1.69 | (3H, s) |
| 10" | 17.67 | $CH_3$ | 1.55 | (3H, s) |
| 1''' | 21.62 | $CH_2$ | 3.26 | (2H, d), $J$=6.6 Hz |
| 2''' | 123.61 | CH | 5.24 | (1H, qt), $J$=1.5, 6.6 Hz |
| 3''' | 131.17 | C | | |
| 4''' | 25.75 | $CH_3$ | 1.61 | (3H, s) |
| 5''' | 17.81 | $CH_3$ | 1.76 | (3H, s) |

FLAVANONE COMPOUND AND USES THEREOF

CROSS-REFERENCE TO RELATED APPLICATIONS

This application claims priority as a divisional application of U.S. patent application Ser. No. 10/562,019, which was filed under 35 U.S.C. §371 from international application PCT/JP2004/008964, filed Jun. 18, 2004. The foregoing are incorporated herein by reference in their entirety.

TECHNICAL FIELD

The present invention relates to a new flavanone compound, and an antioxidant, an antimicrobial agent, an antitumor agent, a food and beverage product, cosmetics, a quasi-drug, and a pharmaceutical each of which contains the flavanone compound.

BACKGROUND ART

As known flavanone compounds, nymphaeol-A, nymphaeol-B, and nymphaeol-C can be enumerated. Regarding these known flavanone compounds, see "K. Yakushijin, K. Shibayama, H. Murata and H. Furukawa: New prenylflavanones from *Hernandia nymphaefolia*(presl) Kubitzki, Heterocycles, 14, 397-402, 1980", "W. R. Phillips, N. J. Baj, A. A. L. Gunatilaka and D. G. I. Kingston: C-Geranyl compounds from *Mimulus clevelandii*, J. Nat. Prod., 59, 495-497, 1996', and "M. H. Tseng, C. H. Chou, Y. M. Chen and Y. H. Kuo: Allelopathic prenylflavanones from the fallen leaves of *Macaranga tanarius*, J. Nat. Prod., 64, 827-828, 2001". Nymphaeol-A is isolated from *Hernandia nymphaefolia* (presl) Kubitzki, or *Mimulus clevelandii*. Nymphaeol-B is isolated from *Hernandia nymphaefolia*(presl) Kubitzki. Nymphaeol-C is isolated from *Hernandia nymphaefolia* (presl) Kubitzki, or *Macaranga tanarius*. However, the physiological activities of these flavanone compounds have been hardly elucidated.

SUMMARY OF THE INVENTION

Accordingly, the present inventors made extensive studies to find the useful physiological activities of a known flavanone compound, and furthermore to find the useful physiological activities of a new flavanone compound by isolating the new flavanone compound. The present invention is based on findings obtained in this manner. It is a first objective of the present invention to provide a new flavanone compound that is utilized for various applications such as food and beverages, and a pharmaceutical. It is a second objective of the present invention to provide applications of a known or new flavanone compound wherein the useful physiological activities of the flavanone compound are utilized.

In order to accomplish the above objectives, one aspect of the present invention provides a flavanone compound represented by the structural formula:

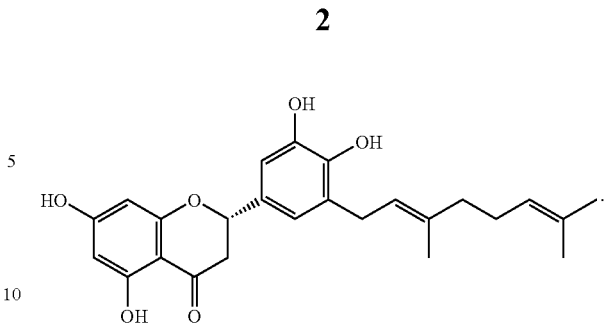

Another aspect of the present invention provides an antioxidant, an antimicrobial agent, an antitumor agent, a food and beverage product, cosmetics, a quasi-drug, and a pharmaceutical each of which contains the flavanone compound as described above.

Still another aspect of the present invention provides an antioxidant, an antimicrobial agent, an antitumor agent, a food and beverage product, cosmetics, a quasi-drug, and a pharmaceutical each of which contains at least one flavanone compound selected from nymphaeol-A, nymphaeol-B, and nymphaeol-C.

BRIEF DESCRIPTION OF THE DRAWINGS

FIG. 1 is a table wherein the physicochemical properties of Compound 1 in Examples are summarized.

FIG. 2 is a table wherein the NMR data of Compound 1 in the Examples are shown.

FIG. 3 is a table wherein the physicochemical properties of Compound 2 in the Examples are summarized.

FIG. 4 is a table wherein the NMR data of Compound 2 in the Examples are shown.

FIG. 5 is a table wherein the physicochemical properties of Compound 3 in the Examples are summarized.

FIG. 6 is a table wherein the NMR data of Compound 3 in Examples are shown.

FIG. 7 is a table wherein the physicochemical properties of Compound 4 in the Examples are summarized.

FIG. 8 is a table wherein the NMR data of Compound 4 in the Examples are shown.

BEST MODE FOR CARRYING OUT THE INVENTION

Hereinafter, a first embodiment of the present invention will be explained.

A flavanone compound according to the first embodiment is 5,7,3',4'-tetrahydroxy-5'-C-geranylflavanone (isonymphaeol-B), which is represented by the structural formula 1:

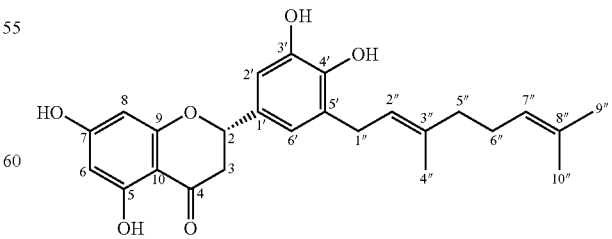

The flavanone compound has the molecular formula $C_{25}H_{28}O_6$, a molecular weight of 424, and a melting point of 123 to 126° C. (see FIG. 3). The flavanone compound is a naturally occurring new compound, which has been isolated from an Okinawa propolis by the present inventors. Although the flavanone compound has a structural characteristic similar to that of eriodictyol, it has a C-geranyl group at the 5'-position. Thus, it is higher in lipophilic properties (or membrane permeabilities) than eriodictyol.

The flavanone compound has as high an anti-oxidant action as eriodictyol or α-tocopherol. In addition, the flavanone compound has an antitumor action which inhibits the proliferation of cancer cells such as a breast cancer cell. Furthermore, the flavanone compound has an action inducing physiological cell-death (or apoptosis) in order to remove undesired cells such as a cancerating abnormal cell, and an aged cell reaching its cellular life span. In addition, the flavanone compound has an antimicrobial action on Gram-positive bacteria such as *Staphylococcus aureus*, and spore forming bacteria such as Genus *Bacillus*.

An antioxidant according to the first embodiment contains the flavanone compound as an active ingredient (or an antioxidant component). The antioxidant may be utilized by adding it to a food and beverage product as a deterioration inhibitor to effectively inhibit deterioration (mainly, oxidation deterioration) of various products, such as the oxidation deterioration of fats and oils, the deterioration of flavor components, the decomposition of a coloring matter, and the discoloration of coloring matter. In a living body wherein a food and beverage product such as a health food product, containing the antioxidant, has been orally ingested, the flavanone compound eliminates active oxygen so as to exert health-enhancement effects such as an enhancement action for hepatic function, a decrease in acetaldehyde toxicity, an antioxidant action for low-density lipoprotein-cholesterol (LDL), an proliferation-inhibiting action to breast cancer cells, and an improvement in immune function. The antioxidant may be utilized by making it contained in cosmetics or a quasi-drug. In that case, it serves for whitening effectiveness and aging protection and the like for the skin, the oral cavity and the like.

An antimicrobial agent according to the first embodiment contains the flavanone compound as an active ingredient. The antimicrobial agent is utilized by adding it to, for example, a food and beverage product. In that case, the food and beverage product is prevented from rotting. The antimicrobial agent may be utilized by adding it to a pharmaceutical, or may be utilized as a pharmaceutical such as a therapeutic drug for infection diseases or an antimicrobial chemotherapeutic remedy. The antimicrobial agent may be utilized by adding it to cosmetics or a quasi-drug. In that case, it serves to keep the skin, the oral cavity, axilla and the like clean.

When the antimicrobial agent is used by adding it to a food and beverage product, a pharmaceutical, cosmetics or a quasi-drug, the concentration of the flavanone compound contained in these products is preferably 10 ppm or more, more preferably 20 ppm or more, still more preferably 30 ppm to 10,000 ppm, and in particular preferably 50 ppm to 1,000 ppm. When the concentration of the flavanone compound is less than 10 ppm, an antimicrobial action can not be satisfactorily exerted. On the contrary, when the concentration is more than 10,000 ppm, it is uneconomical.

An antitumor agent according to the first embodiment contains the flavanone compound as an active ingredient, which is mainly utilized as a pharmaceutical. The dose of the antitumor agent is determined so that the concentration of the flavanone compound acts upon cancer cells can be preferably 0.1 µM to 100 mM, and more preferably 10 to 1,000 µM. When the concentration of the flavanone compound is less than 0.1 µM, the therapeutic effect is weak. On the contrary, when the concentration is more than 100 mM, it is uneconomical.

The dose of the antitumor agent for an adult is preferably 0.5 to 10 g, and more preferably 2 to 5 g in terms of the flavanone compound per day. When the daily dose of the flavanone compound is less than 0.5 g, its antitumor action can not be satisfactorily exerted. On the contrary, when the daily dose is more than 10 g, it is uneconomical. The dose of the antitumor agent for a child is preferably about half of that for an adult.

When the flavanone compound is contained in a food and beverage product (for example, a health food product), cosmetics or a quasi-drug, those products may be utilized as products which exert cancer-preventive effects by promoting the physiological removal of undesired cells such as a cancerating abnormal cell. When the product is a pharmaceutical, the concentration of the flavanone compound therein is preferably about 1 to 50%, and more preferably about 10 to 30%.

A food and beverage product according to the first embodiment contains the flavanone compound. The food and beverage product may contain the antioxidant or antimicrobial agent as mentioned above. Due to the antioxidant action of the flavanone compound contained in the food and beverage product, the food and beverage product removes active oxygen in vivo, and thus is utilized as a health food which exerts various health-enhancement effects. The flavanone compound in the food and beverage product also prevents the deterioration of the food and beverage product due to the deterioration-inhibiting action of the flavanone compound so as to enhance the storage stability of the food and beverage product, or prevents the food and beverage product from rotting due to the antimicrobial action of the flavanone compound so as to enhance the storage stability of the food and beverage product. Therefore, the quality of the food and beverage product is stably maintained over a long period of time. The flavanone compound in the food and beverage product promotes, by its antitumor action, the physiological removal of undesired cells such as a cancerating abnormal cell and an aged cell reaching its cellular life span. Thus the food and beverage product is also utilized as a health food which exerts a high health-enhancement effect.

The intake of the food and beverage product for an adult is preferably 0.05 to 10 g, and more preferably 0.2 to 5 g in terms of the flavanone compound per day. When the daily intake of the flavanone compound is less than 0.05 g, the antioxidant action of the flavanone compound may not be effectively exerted. On the contrary, when the daily intake is more than 10 g, it is uneconomical.

The first embodiment has the following advantageous effects.

A flavanone compound of the first embodiment is 5,7,3',4'-tetrahydroxy-5'-C-geranylflavanone (isonymphaeol-B) represented by the structural formula 1 mentioned above. Since the flavanone compound has an antioxidant action, an antitumor action, an antimicrobial action and the like, it is used for a wide variety of applications, including a food and beverage product and a pharmaceutical. In particular, the flavanone compound, which is a single compound, can simultaneously exert a multiple and multivalent action. Thus, the point that the flavanone compound is utilized as a raw material for a multifunctional health-food as typified by a propolis product is worthy of note. Furthermore, the flavanone compound is used for a similar application as the one for eriodictyol, as well as for various applications wherein a higher lipophilic property than that of eriodictyol is utilized. Since the flavanone compound is contained in a propolis product which has been conventionally used as a health-food raw-material, there is no problem with respect to oral ingestion and transcutaneous administration.

An antioxidant of the first embodiment contains the flavanone compound having a high antioxidant action, as an active ingredient. Therefore, the antioxidant, when added to a food and beverage product, cosmetics or a quasi-drug, prevents the deterioration thereof so as to enhance the storage stability, as well as exerting a health-enhancement effect and an anti-aging effect in vivo when the antioxidant has been orally ingested or transcutaneously administered.

An antimicrobial agent of the first embodiment contains the flavanone compound having a high antimicrobial action, as an active ingredient. Therefore, the antimicrobial agent, when added to a food and beverage product, cosmetics or a quasi-drug, prevents deterioration thereof so as to enhance the storage stability, as well as exerting a high sanitary effect and a high deodorant effect when the antimicrobial agent has been transcutaneously administered as cosmetics or a quasi-drug. The antimicrobial agent is also utilized as a pharmaceutical.

An antitumor agent of the first embodiment contains the flavanone compound having a high antitumor action, as an active ingredient. Therefore, the antitumor agent exerts a high curative effect on a cancer, as well as being expected to exert a preventive effect thereon.

A food and beverage product (a beverage or a food product) of the first embodiment contains the flavanone compound having an antioxidant action, an antitumor action, an antimicrobial action and the like. Therefore, according to the food and beverage product, deterioration and rottenness of the food and beverage product itself is prevented, as well as multiple and useful effects in vivo, such as a health-enhancement effect, an anti-aging effect, a metabolism-enhancement effect and a cancer-preventive effect, are simultaneously exerted. When the content of the flavanone compound in a food and beverage product is set in a relatively small amount, a food and beverage product whose storage stability only has been enhanced by the deterioration-preventive or rottenness-preventive action of the flavanone compound is easily obtained.

Hereinafter, a second embodiment of the present invention will be explained.

A flavanone compound according to the second embodiment contains at least one substance selected from nymphaeol-A, nymphaeol-B, and nymphaeol-C.

Nymphaeol-B is 5,7,3',4'-tetrahydroxy-2'-C-geranylflavanone and is represented by the structural formula 2:

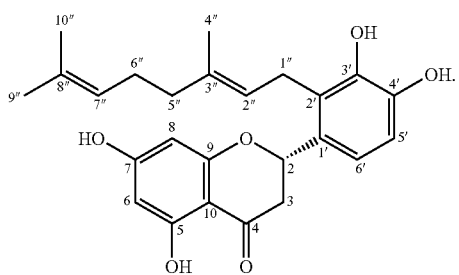

Nymphaeol-B has the molecular formula $C_{25}H_{28}O_6$, a molecular weight of 424, and a melting point (MP) of 80 to 83° C. (see FIG. 1). Nymphaeol-B is a naturally occurring organic compound, which has been isolated from an Okinawa propolis by the present inventors. Although nymphaeol-B has a structural characteristic similar to that of eriodictyol, it has a C-geranyl group at the 2'-position. Thus, it is higher in lipophilic properties (or membrane permeabilities) than eriodictyol.

Nymphaeol-A is 5,7,3',4'-tetrahydroxy-6-C-geranylflavanone and is represented by the structural formula 3:

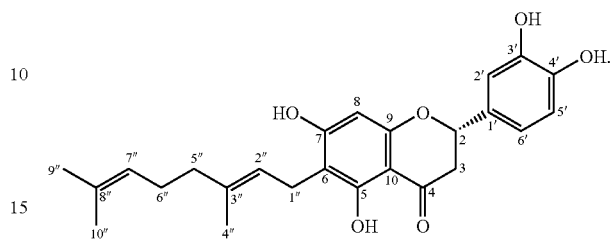

Nymphaeol-A has the molecular formula $C_{25}H_{28}O_6$, a molecular weight of 424, and a melting point (MP) of 172 to 175° C. (see FIG. 5). Nymphaeol-A is a naturally occurring organic compound, which has been isolated from an Okinawa propolis by the present inventors. Although nymphaeol-A has a structural characteristic similar to that of eriodictyol, it has a C-geranyl group at the 6-position. Thus, it is higher in lipophilic properties (or membrane permeabilities) than eriodictyol.

Nymphaeol-C is 5,7,3',4'-tetrahydroxy-6-(3''',3'''-dimethylallyl)-2'-C-geranylflavanone and is represented by the structural formula 4:

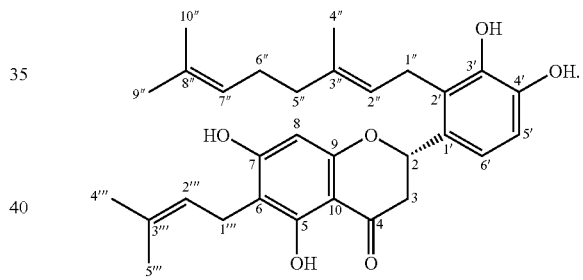

Nymphaeol-C has the molecular formula $C_{30}H_{36}O_6$, and a molecular weight of 492 (see FIG. 7). Nymphaeol-C is a naturally occurring organic compound, which has been isolated from an Okinawa propolis by the present inventors. Although nymphaeol-C has a structural characteristic similar to that of eriodictyol, it has a 3''',3'''-dimethylallyl group at the 6-position as well as a C-geranyl group at the 2'-position. Thus, nymphaeol-C is higher in lipophilic properties (or membrane permeabilities) than eriodictyol, nymphaeol-A and nymphaeol-B.

Any of nymphaeol-A, nymphaeol-B and nymphaeol-C has as high an antioxidant action as eriodictyol or α-tocopherol. Furthermore, any of nymphaeol-A, nymphaeol-B and nymphaeol-C has an antitumor action which inhibits the proliferation of cancer cells such as a breast cancer cell. The antitumor action of each of nymphaeol-A and nymphaeol-C is higher than that of nymphaeol-B. Each of nymphaeol-A, nymphaeol-B and nymphaeol-C has an action inducing physiological cell-death (apoptosis) in order to remove undesired cells such as a canceratting abnormal cell, and an aged cell reaching its cellular life span. In addition, nymphaeol-B has an antimicrobial action on Gram-positive bacteria such as *Staphylococcus aureus*, and spore forming bacteria such as Genus *Bacillus*. Each of nymphaeol-A and nymphaeol-C has an antimicrobial action on Gram-negative bacteria such as *Escherichia coli*, and the above-mentioned Gram-positive bacteria and spore forming bacteria.

An antioxidant according to the second embodiment contains at least one kind selected from nymphaeol-A, nymphaeol-B and nymphaeol-C as an active ingredient (or an anti-oxidant component). The antioxidant may be utilized by adding it to a food and beverage product as a deterioration inhibitor to effectively inhibit the deterioration (mainly, oxidation deterioration) of various products, such as the oxidation deterioration of fats and oils, the deterioration of flavor components, the decomposition of coloring matter, and the discoloration of coloring matter. In a living body wherein a food and beverage product such as a health food, containing the antioxidant, has been orally ingested, each of nymphaeol-A, nymphaeol-B and nymphaeol-C eliminates active oxygen so as to exert health-enhancement effects such as an enhancement action for hepatic function, a decrease in acetaldehyde toxicity, an antioxidant action for low-density lipoprotein-cholesterol (LDL), an proliferation-inhibiting action to breast cancer cells, and an improvement in immune function. The antioxidant may be utilized by allowing it to be contained in cosmetics or a quasi-drug. In that case, it serves for whitening effectiveness and aging protection and the like for the skin, the oral cavity and the like.

An antimicrobial agent according to the second embodiment contains at least one substance selected from nymphaeol-A, nymphaeol-B and nymphaeol-C as an active ingredient. The antimicrobial agent is utilized by adding it to, for example, a food and beverage product. In that case, the food and beverage product is prevented from rotting. The antimicrobial agent may be utilized by adding it to a pharmaceutical, or may be utilized as a pharmaceutical such as a therapeutic drug for infection diseases or an antimicrobial chemotherapeutic remedy. The antimicrobial agent may be utilized by adding it to cosmetics or a quasi-drug. In that case, it serves to keep the skin, the oral cavity, axilla and the like clean.

When the antimicrobial agent is used by adding it to a food and beverage product, a pharmaceutical, cosmetics or a quasi-drug, the total concentration of nymphaeol-A, nymphaeol-B and nymphaeol-C contained in these products is preferably 10 ppm or more, more preferably 15 ppm or more, still more preferably 30 ppm to 10,000 ppm, and in particularly preferably 50 ppm to 1,000 ppm. When the total concentration thereof is less than 50 ppm, antimicrobial action can not be satisfactorily exerted. On the contrary, when the concentration is more than 10,000 ppm, it is uneconomical.

An antitumor agent according to the second embodiment contains at least one substance selected from nymphaeol-A, nymphaeol-B and nymphaeol-C as an active ingredient, which is mainly utilized as a pharmaceutical. The dose of the antitumor agent is determined so that the total concentration of nymphaeol-A, nymphaeol-B and nymphaeol-C when nymphaeol-A, nymphaeol-B and nymphaeol-C act upon cancer cells can be preferably 0.1 µM to 100 mM, and more preferably 10 to 1,000 µM. When the total concentration thereof is less than 0.1 µM, the therapeutic effect is weak. On the contrary, when it is more than 100 mM, it is uneconomical.

The dose of the antitumor agent for an adult is preferably 0.5 to 10 g, and more preferably 2 to 5 g in terms of nymphaeol-A, nymphaeol-B and nymphaeol-C per day. When the daily dose of nymphaeol-A, nymphaeol-B and nymphaeol-C is less than 0.5 g, their antitumor actions can not be satisfactorily exerted. On the contrary, when it is more than 10 g, it is uneconomical. The dose of nymphaeol-A, nymphaeol-B and nymphaeol-C for a child is preferably about half of that for an adult.

When at least one substance selected from nymphaeol-A, nymphaeol-B and nymphaeol-C is contained in a food and beverage product (for example, a health food product), cosmetics or a quasi-drug, those products may be utilized as products that exert cancer-preventive effects by promoting the physiological removal of undesired cells such as a cancerating abnormal cell. When the product is a pharmaceutical, the total concentration of nymphaeol-A, nymphaeol-B and nymphaeol-C therein is preferably about 1 to 50%, and more preferably about 10 to 30%.

A food and beverage product according to the second embodiment contains at least one substance selected from nymphaeol-A, nymphaeol-B and nymphaeol-C. The food and beverage product may be contains the antioxidant or antimicrobial agent as mentioned above. Due to the antioxidant action of nymphaeol-A, nymphaeol-B and nymphaeol-C contained in the food and beverage product, the food and beverage product removes active oxygen in vivo, and thus is utilized as a health food which exerts various health-enhancement effects. Nymphaeol-A, nymphaeol-B and nymphaeol-C in the food and beverage product also prevents the deterioration of the food and beverage product due to the deterioration-inhibiting action thereof so as to enhance the storage stability of the food and beverage product, or prevents the food and beverage product from rotting due to the antimicrobial action thereof so as to enhance the storage stability of the food and beverage product. Therefore, the quality of the food and beverage product is stably maintained over a long period of time. Nymphaeol-A, nymphaeol-B and nymphaeol-C in the food and beverage product promotes, by their antitumor actions, the physiological removal of undesired cells such as a cancerating abnormal cell and an aged cell reaching its cellular life span. Thus, the food and beverage product is also utilized as a health food which exerts a high health-enhancement effect.

The intake of the food and beverage product for an adult is preferably 0.05 to 10 g, and more preferably 0.2 to 5 g in terms of nymphaeol-A, nymphaeol-B and nymphaeol-C per day. When the daily intake of nymphaeol-A, nymphaeol-B and nymphaeol-C is less than 0.05 g, the antioxidant action thereof may not be effectively exerted. On the contrary, when the daily intake is more than 10 g, it is uneconomical.

The second embodiment has the following advantageous effects.

Since any of nymphaeol-A, nymphaeol-B and nymphaeol-C has an antioxidant action, an antitumor action and an antimicrobial action, it is used for a wide variety of applications, including a food and beverage product and a pharmaceutical. In particular, each of nymphaeol-A, nymphaeol-B and nymphaeol-C, which is a single compound, can simultaneously exert a multiple and multivalent action. Thus, the point that each of nymphaeol-A, nymphaeol-B and nymphaeol-C is utilized as a raw material for a multifunctional health-food as typified by a propolis product is worthy of note. Furthermore, nymphaeol-A, nymphaeol-B and nymphaeol-C is used for a similar application to the one for eriodictyol, as well as for various applications wherein a higher lipophilic property than that of eriodictyol is utilized. Since nymphaeol-A, nymphaeol-B or nymphaeol-C is contained in a propolis product which has been conventionally used as a raw material for health food products, there is no problem with respect to oral ingestion and transcutaneous administration.

An antioxidant of the second embodiment contains, as an active ingredient, at least one substance selected from nymphaeol-A, nymphaeol-B and nymphaeol-C, each of which has a high antioxidant action. Therefore, the antioxidant, when added to a food and beverage product, cosmetics or a quasi-drug, prevents the deterioration thereof so as to enhance the storage stability, as well as exerts a health-enhancement effect and an anti-aging effect in vivo when the antioxidant has been orally ingested or transcutaneously administered.

An antimicrobial agent of the second embodiment contains, as an active ingredient, at least one substance selected from nymphaeol-A, nymphaeol-B and nymphaeol-C, each of which has a high antimicrobial action. Therefore, the antimicrobial agent, when added to a food and beverage product, cosmetics or a quasi-drug, prevents deterioration thereof so as to enhance storage stability, as well as exerts a high sanitary effect and a high deodorant effect when the antimicrobial agent has been transcutaneously administered as cosmetics or a quasi-drug. The antimicrobial agent is also utilized as a pharmaceutical.

An antitumor agent of the second embodiment contains, as an active ingredient, at least one substance selected from nymphaeol-A, nymphaeol-B and nymphaeol-C, each of which has a high antitumor action. Therefore, the antitumor agent exerts a high curative effect on a cancer, as well as is expected to exert a preventive effect thereon.

A food and beverage product (a beverage or food product) of the second embodiment contains at least one substance selected from nymphaeol-A, nymphaeol-B and nymphaeol-C, each of which has an antioxidant action, an antitumor action, an antimicrobial action and the like. Therefore, according to the food and beverage product, the deterioration and rottenness of the food and beverage product itself are prevented, as well as multiple and useful effects in vivo, such as a health-enhancement effect, an anti-aging effect, a metabolism-enhancement effect and a cancer-preventive effect, are simultaneously exerted. When the content of nymphaeol-A, nymphaeol-B and nymphaeol-C in a food and beverage product is set in a relatively small amount, a food and beverage product whose storage stability only has been enhanced by the deterioration-preventive or rottenness-preventive action of nymphaeol-A, nymphaeol-B and nymphaeol-C is easily obtained.

Hereinafter, the present invention will be more specifically explained by reference to Examples.

<Isolation of Compounds>

To 50 g of an Okinawa propolis raw material, 500 ml of ethanol was added, followed by an ultrasonic treatment for several minutes. The solution was stirred at room temperature overnight, and the residual material was removed through filtration. The resultant extract was concentrated under reduced pressure to obtain 39.73 g of an ethanol extract. Thereafter, the ethanol extract was subjected to column chromatography under the condition as described below, whereby eleven fractions were obtained, which were eluted with the elution solvents of the following (1) to (11).

Column Tube: glass column, 5.0×45 cm
Filler: silica gel, approximately 590 cm$^3$
Elution Solvents:
(1) hexane:ethyl acetate=90:10 (350 ml)
(2) hexane:ethyl acetate=80:20 (220 ml)
(3) hexane:ethyl acetate=70:30 (250 ml)
(4) hexane:ethyl acetate=60:40 (1000 ml)
(5) hexane:ethyl acetate=50:50 (200 ml)
(6) hexane:ethyl acetate=40:60 (100 ml)
(7) hexane:ethyl acetate=30:70 (100 ml)
(8) hexane:ethyl acetate=20:80 (100 ml)
(9) hexane:ethyl acetate=10:90 (100 ml)
(10) ethyl acetate (200 ml)
(11) methanol (700 ml)

When each of the obtained fractions was analyzed under the following HPLC condition 1, it has been confirmed that four main ingredients are contained in the fraction (referred to as "the fourth fraction") which was eluted with the elution solvent (4).

HPLC Condition 1
Column: YMC-Pack R&D ODS (4.6×250 mm)
Solvent: A: water (with 2% of acetic acid),
B: acetonitrile (with 2% of acetic acid)
Elution Condition:
0-60 min (gradient elution; A:B=80:20→20:80)
Flow Rate: 1 ml/min
Detection: UV 280 nm Then, the fourth fraction was used so as to separate and purify it under the following HPLC condition 2, whereby Compound 1 (yield: 61.1 mg), Compound 2 (yield: 65.7 mg) and Compound 3 (yield: 99.8 mg) were isolated. Furthermore, the fourth fraction was used so as to separate and purify it under the following HPLC condition 3, whereby Compound 4 (yield: 20.0 mg) was isolated.

HPLC Condition 2
Column: YMC-Pack R&D ODS (20×250 mm)
Solvent: water (with 0.1% of TFA): acetonitrile
(with 0.1% of TFA)=40:60
Flow Rate: 9 ml/min
Detection: UV 280 nm HPLC Condition 3
Column: YMC-Pack R&D ODS (20×250 mm)
Solvent: water (with 0.1% of TFA): acetonitrile
(with 0.1% of TFA)=20:80
Flow Rate: 9 ml/min
Detection: UV 280 nm <Identification of Compounds 1 to 4>

The structure of each of Compounds 1 to 4 was analyzed by using $^1$H-NMR, $^{13}$C-NMR, MS, IR spectrum, UV spectrum, and the like.

(Compound 1)

The physicochemical properties of Compound 1 are shown in FIG. 1. From the ESI-MS measurement, it was confirmed that the molecular weight of Compound 1 was 424. From the IR spectrum, it was suggested that there were a hydroxyl group at 3420 cm$^{-1}$ and a carbonyl group at 1680 cm$^{-1}$, and the UV spectrum showed a characteristic spectrum of flavanone or flavanol, whereby Compound 1 was presumed to have a flavanone skeleton. From the integrated value of the $^1$H-NMR spectrum, the existence of 28 protons was identified, while from the $^{13}$C-NMR spectrum, 25 signals were observed. From the DEPT spectrum, three methyl groups, four methylene groups, seven methine groups and eleven quaternary-carbon atoms were identified. From the results mentioned above, the molecular formula of Compound 1 was presumed to be $C_{25}H_{28}O_6$. Furthermore, from the NMR data shown in FIG. 2, concerning the HSQC spectrum, the $^1$H—$^1$H COSY, the HMBC spectrum, the CD spectrum, and the like, Compound 1 was identified as nymphaeol-B (5,7,3', 4'-tetrahydroxy-2'-C-geranylflavanone) represented by the structural formula (2) mentioned above. Although the isolation of this compound from *Hernandia nymphaefolia*(presl) Kubitzki has been already reported, the isolation of this compound from propolis has been carried out by this study for the first time.

(Compound 2)

The physicochemical properties of Compound 2 are shown in FIG. 3. From the ESI-MS measurement, it was confirmed that the molecular weight of Compound 2 was 424. From the IR spectrum, it was suggested that there were a hydroxyl group at 3360 cm$^{-1}$ and a carbonyl group at 1680 cm$^{-1}$, and the UV spectrum showed a characteristic spectrum of flavanone or flavanol, whereby Compound 2 was presumed to have a flavanone skeleton. From the integrated value of the $^1$H-NMR spectrum, the existence of 28 protons was confirmed, while from the $^{13}$C-NMR spectrum, 25 signals were observed. From the DEPT spectrum, three methyl groups, four methylene groups, eight methine groups and eleven quaternary-carbon atoms were identified. From the results mentioned above, the molecular formula of Compound 2 was presumed to be $C_{25}H_{28}O_6$. Furthermore, from the NMR data shown in FIG. 4, concerning the HSQC spectrum, the $^1$H—$^1$H COSY, the HMBC spectrum, the CD spectrum, and the like, Compound 2 was identified as 5,7,3',4'-tetrahydroxy-5'-C-geranylflavanone represented by the structural formula (1) mentioned above. This compound was a new compound which had not been heretofore disclosed in the literature or the like.

(Compound 3)

The physicochemical properties of Compound 3 are shown in FIG. 5. From the ESI-MS measurement, it was confirmed that the molecular weight of Compound 3 was 424. From the IR spectrum, it was suggested that there were a hydroxyl group at 3380 cm$^{-1}$ and a carbonyl group at 1680 cm$^{-1}$, and the UV spectrum showed a characteristic spectrum of flavanone or flavanol, whereby Compound 3 was presumed to have a flavanone skeleton. From the integrated value of the $^1$H-NMR spectrum, the existence of 28 protons was confirmed, while from the $^{13}$C-NMR spectrum 25 signals were observed. From the DEPT spectrum, the existence of three methyl groups, four methylene groups, seven methine groups and eleven quaternary-carbon atoms was confirmed. From the results mentioned above, the molecular formula of Compound 3 was presumed to be $C_{25}H_{28}O_6$. Furthermore, from the NMR data shown in FIG. 6, concerning the HSQC spectrum, the $^1$H—$^1$H COSY, the HMBC spectrum, the CD spectrum, and the like, Compound 3 was identified as nymphaeol-A (5,7,3',4'-tetrahydroxy-6-C-geranylflavanone) represented by the structural formula (3) mentioned above. Although the isolation of this compound from *Hernandia nymphaefolia*(presl) Kubitzki and *Mimulus clevelandii* has been already reported, the isolation of this compound from propolis has been carried out by this study for the first time.

(Compound 4)

The physicochemical properties of Compound 4 are shown in FIG. 7. From the FAB-MS measurement, it was confirmed that the molecular weight of Compound 4 was 492. From the IR spectrum, it was suggested that there were a hydroxyl group at 3400 cm$^{-1}$ and a carbonyl group at 1640 cm$^{-1}$, and the UV spectrum showed a characteristic spectrum of flavanone or flavanol, whereby Compound 4 was presumed to have a flavanone skeleton. From the integrated value of the $^1$H-NMR spectrum, the existence of 36 protons was confirmed, while from the $^{13}$C-NMR spectrum, the existence of 30 carbon atoms was observed. From the DEPT spectrum, the existence of five methyl groups, five methylene groups, seven methylene groups, and thirteen quaternary-carbon atoms was confirmed. From the results mentioned above, the molecular formula of Compound 4 was presumed to be $C_{30}H_{36}O_6$. Furthermore, from the NMR data shown in FIG. 8, concerning the HSQC spectrum, the $^1$H—$^1$H COSY, the HMBC spectrum, the CD spectrum, and the like, Compound 4 was identified as nymphaeol-C (5,7,3',4'-tetrahydroxy-6-(3''',3'''-dimethylallyl)-2'-C-geranylflavanone) represented by the structural formula (4) mentioned above. Although the isolation of this compound from *Hernandia nymphaefolia*(presl) Kubitzki, and *Macaranga tanarius* has been already reported, the isolation of this compound from propolis has been carried out by this study for the first time.

<Measurement of Contents in Propolis>

With respect to the fact of how much of Compounds 1 to 4 are contained in an Okinawa propolis, analysis was conducted under the following HPLC condition 4 so as to determine the content of each of Compounds 1 to 4. As a result, it has been confirmed that 12.7 g of Compound 1, 10.5 g of Compound 2, 13.5 g of Compound 3, and 9.1 g of Compound 4 are contained in 100 g of raw material of Okinawa propolis.

HPLC Condition 4

Column: YMC-Pack R&D ODS (4.6×250 mm)

Solvent: A: water (with 0.1% of TFA),

B: acetonitrile (with 0.1% of TFA)

Elution Conditions 0-50 min (gradient elution; A:B=65:35→0:100)

Flow Rate: 1 ml/min

Detection: UV 280 nm

<DPPH Radical Scavenging Activity Test>

DPPH (α,α-diphenyl-β-picrylhydradil) is a purple stable radical having a maximum absorption at 517 nm, which is converted into colorless hydrazine by gaining hydrogen. This color reaction was utilized so as to determine the radical scavenging activity of each of Compounds 1 to 4 and the like. That is, each of Compounds 1 to 4 was dissolved in ethanol to prepare 3 ml of a sample solution having a concentration of 25 µM. Thereafter, to each of the resultant sample solutions, 0.75 ml of a 0.5 mM DPPH solution (whose solvent was ethanol) was added and stirred, and reacted in a dark place for one hour, followed by the determination of an absorbance at 517 nm. Furthermore, in place of Compounds 1 to 4, BHT (butylated hydroxytoluene), α-tocopherol or eriodictyol was used so as to determine an absorbance according to a similar procedure to the above. Besides, instead of the above sample solutions, ethanol was used as a control so as to determine an absorbance according to a similar procedure to the above. Then the radical scavenging activity (%) of each of the materials was calculated using the following calculation formula 1. The results are shown in the following Table 1. Incidentally, each of values shown in Table 1 is the average value and standard deviation of values obtained from three runs.

(Radical Scavenging Activity)=[{(Absorbance of Control)−(Absorbance of Sample Solution)}/(Absorbance of Control)]×100      Calculation Formula 1

TABLE 1

| Sample | Radical Scavenging Activity (%) from DPPH Radical Scavenging Activity Test | Antioxidant Activity (%) from β-carotene Fading Test |
|---|---|---|
| Compound 1 | 55.35 ± 0.43 | 85.54 ± 2.24 |
| Compound 2 | 49.86 ± 0.96 | 78.07 ± 1.79 |
| Compound 3 | 64.00 ± 0.58 | 60.62 ± 1.16 |
| Compound 4 | 50.79 ± 0.08 | 80.06 ± 0.29 |
| BHT | 28.51 ± 7.48 | 85.02 ± 1.89 |
| α-tocopherol | 58.87 ± 1.24 | 93.00 ± 0.73 |
| Eriodictyol | 68.82 ± 1.12 | 81.47 ± 2.48 |

From the results shown in Table 1, it has been clarified that each of Compounds 1 to 4 has a higher radical scavenging activity than that of BHT, and has about the same radical scavenging activity as that of α-tocopherol. Among others, Compound 3 had the highest radical scavenging activity, which was about the same as that of eriodictyol. Although each of Compounds 1, 3 and 4 is a known material, the radical scavenging activity thereof has not been conventionally studied. The remarkably high radical scavenging activity of each of Compounds 1, 3 and 4 has been clarified by this study for the first time.

<β-carotene Fading Test>

β-carotene will fade due to the reaction of linoleic acid peroxide, which is produced by the autoxidation of linoleic acid, with a double bond in β-carotene. This phenomenon was utilized so as to determine the antioxidant activity of each of Compounds 1 to 4 and the like. That is, first of all, 2 ml of a 200 mg/ml solution of Tween-40 in chloroform, 0.4 ml of a 100 mg/ml solution of linoleic acid in chloroform, and 3 ml of a 0.1 mg/ml solution of β-carotene in chloroform were mixed, and thereafter the solvent was removed by using a nitrogen gas. Subsequently, 100 ml of distilled water was added thereto, and adequately stirred to obtain an emulsion. To 3 ml of this emulsion, ethanol was added to completely dissolve the solute in the solvent. Thereafter, each of Compounds 1 to 4 was dissolved in ethanol so as to prepare a sample solution having a concentration of 1.2 mM. 50 µl of the sample solution was mixed with the above emulsion wherein the solute had been completely dissolved so as to prepare a reaction liquid (or a sample reaction liquid). Then the concentration of each of Compounds 1 to 4 in the reaction liquid was 20 µM. The reaction liquid was incubated at 60° C. for 60 minutes. Then the absorbance of each of the reaction liquid before the incubation and the reaction liquid after the incubation was determined at 470 nm. Furthermore, BHT, α-tocopherol, or eriodictyol was used in place of Compounds 1 to 4 so as to determine the absorbance of the reaction liquid before and after incubation according to a similar procedure to the above-mentioned one. In addition, as a control, a reaction liquid (or a control reaction liquid) wherein no sample solution was contained was prepared so as to determine the absorbance of the reaction liquid before and after incubation according to a similar procedure to the above-mentioned one. The antioxidant activity (%) of each of the materials was calculated using the following calculation formula 2. The results are shown in Table 1 described above. Incidentally, each of values shown in Table 1 is the average value and standard deviation of values obtained from three runs.

(Antioxidant Activity)=[{(Fading Rate of Control)–(Fading Rate of Sample Solution)}/(Fading Rate of Control)]×100      Calculation Formula 2

It should be noted that in the calculation formula 2, "Fading Rate of Control" is the natural logarithm of a value which is acquired by dividing the absorbance of the control reaction liquid before incubation by the absorbance of the control reaction liquid after incubation and further by dividing the resultant value by 60; and "Fading Rate of Sample Solution" is the natural logarithm of a value which is acquired by dividing the absorbance of the sample reaction liquid before incubation by the absorbance of the sample reaction liquid after incubation and further by dividing the resultant value by 60.

From the results as shown in Table 1, it has been confirmed that Compound 2 has about the same high antioxidant activity as that of each of BHT, α-tocopherol, and eriodictyol.

From the results as shown in Table 1, it has been confirmed that any of Compounds 1 to 4 has a high antioxidant activity, and among them, Compounds 1, 2 and 4 have about the same high antioxidant activity as that of each of BHT, α-tocopherol, and eriodictyol. Although each of Compounds 1, 3 and 4 is a known material, the antioxidant activity thereof has not been conventionally studied. The remarkably high antioxidant activity of each of Compounds 1, 3 and 4 has been clarified by this study for the first time.

<Breast Cancer Cell Proliferation-Inhibition Test>

When breast cancer cells (MCF-7) are cultured, if estradiol (or 17β-estradiol) having a cell-proliferation accelerating action, is added thereto, the proliferation of breast cancer cells can be simply promoted in a short period. This phenomenon was utilized so as to examine the effect of each of Compounds 1 to 4 and the like on the proliferation inhibition of breast cancer cells. That is, first of all, each of Compounds 1 to 4 was diluted with dimethyl sulfoxide to prepare a sample solution. Thereafter, $2 \times 10^3$ of MCF-7 were inoculated in each well of a 96-well plate, and estradiol and the sample solution were added thereto after 4 hours. Estradiol was added to each compartment so that the final concentration of estradiol can be 0.1 nM, and the final concentration of the sample solution can be 0.2 µM, 2 µM, or 20 µM. After incubation for a predetermined period of time (three or five days), each of the media was replaced with a new medium, and an enzyme solution (Cell counting Kit-8: Wako) was added to the new medium in an amount of 10% of the new medium. After maintained the medium in an incubator at a temperature of 37° C. for two hours, the absorbance of the medium was determined at a wavelength of 450 nm (a reference wave length of 630 nm) by means of a spectrophotometer so as to quantify the number of living cells in each compartment.

As for the compartment whose incubation period is predetermined to be five days, on the third day of the incubation, the medium was replaced with a new medium, and thereafter, estradiol and a sample solution were added to the new medium, and the incubation was continued till fifth day. As for the compartment whose incubation period is predetermined to be 0 day, at four hours after the cells were inoculated, an enzyme solution was added to the medium. The medium was maintained in an incubator at a temperature of 37° C. for two hours, followed by determining the absorbance.

Instead of Compounds 1 to 4, eriodictyol was used to determine the absorbance according to a similar procedure to the above-mentioned one, and thus the number of living cells in each compartment was quantified. Furthermore, Control 1 to which neither estradiol nor a sample had been added was used to determine the absorbance according to a similar procedure to the above-mentioned one, and thus the number of living cells in each compartment was quantified, while Control 2 to which no sample had been added was used to determine the absorbance according to a similar procedure to the above-mentioned one, and thus the number of living cells in each compartment was quantified.

When it is assumed that the number of living cells of Control 1 as quantified after a zero-day incubation period is 1, the relative value of living cells as quantified in each of the runs mentioned above is shown in Table 2. Incidentally, each of values shown in Table 2 is the average value and standard deviation of values obtained from eight wells.

TABLE 2

| | Relative Value of Living Cells | | |
|---|---|---|---|
| Sample | On 0-day Incubation | After 3-days Incubation Period | After 5-days Incubation Period |
| Control 1 | 1.00 ± 0.07 | 2.45 ± 0.12 | 3.29 ± 0.08 |
| Control 2 (0.1 nM Estradiol) | 0.97 ± 0.04 | 3.12 ± 0.34 | 7.02 ± 0.99 |

TABLE 2-continued

| Sample | | On 0-day Incubation | After 3-days Incubation Period | After 5-days Incubation Period |
|---|---|---|---|---|
| Eriodictyol | 0.2 μM | 0.96 ± 0.04 | 2.88 ± 0.22 | 7.33 ± 0.60 |
| | 2 μM | 0.98 ± 0.07 | 2.90 ± 0.13 | 7.16 ± 0.36 |
| | 20 μM | 1.01 ± 0.05 | 2.54 ± 0.30 | 5.13 ± 0.62 |
| Compound 1 | 0.2 μM | 0.98 ± 0.04 | 2.86 ± 0.14 | 7.26 ± 0.48 |
| | 2 μM | 0.99 ± 0.05 | 2.58 ± 0.11 | 6.01 ± 0.25 |
| | 20 μM | 1.01 ± 0.05 | 2.22 ± 0.19 | 4.17 ± 0.50 |
| Compound 2 | 0.2 μM | 0.95 ± 0.04 | 2.97 ± 0.37 | 6.83 ± 0.58 |
| | 2 μM | 0.99 ± 0.04 | 2.68 ± 0.19 | 6.59 ± 0.50 |
| | 20 μM | 1.00 ± 0.07 | 2.59 ± 0.21 | 5.59 ± 1.01 |
| Compound 3 | 0.2 μM | 0.99 ± 0.05 | 2.94 ± 0.20 | 6.99 ± 0.66 |
| | 2 μM | 1.01 ± 0.05 | 2.53 ± 0.30 | 5.38 ± 0.44 |
| | 20 μM | 0.96 ± 0.04 | 1.21 ± 0.22 | 0.89 ± 0.12 |
| Compound 4 | 0.2 μM | 0.99 ± 0.04 | 2.97 ± 0.27 | 6.30 ± 0.54 |
| | 2 μM | 1.00 ± 0.07 | 3.03 ± 0.30 | 6.41 ± 0.53 |
| | 20 μM | 0.98 ± 0.04 | 1.27 ± 0.20 | 1.01 ± 0.12 |

From the results shown in Table 2, it has been confirmed that each of Compounds 1 to 4 has the effect of inhibiting the proliferation of breast cancer cells with differences somewhat therebetween. Furthermore, it has been found that the effect of each of Compounds 1 to 4 on inhibiting the proliferation of breast cancer cells depends upon its concentration. In particular, as for compartments to which 20 μM of Compound 3 or 4 had been added, a more strongly inhibiting effect on the proliferation of breast cancer cells (i.e., a cytotoxic effect upon breast cancer cells) than that of Control 1 was confirmed. Although each of Compounds 1, 3 and 4 is a known material, the breast cancer cells proliferation inhibiting action thereof has not been conventionally studied. The remarkably high antitumor activity of each of Compounds 1, 3 and 4 has been clarified by this study for the first time.

<Antimicrobial Activity Test with Ethanol Extract>

*E. coli* (IFO3366) as a biological indicator for Gram-negative bacteria; *Staphylococcus aureus* (IFO15035) as a biological indicator for Gram-positive bacteria; *Bacillus cereus* (IFO15305T) as a biological indicator for spore forming bacteria having resistance properties even to a process such as thermal sterilization; and *Bacillus coagulans* separated from a deteriorated canned food, as a biological indicator for fungi which cause the deterioration of a canned food were used so as to evaluate the antimicrobial activity of each of Compounds 1 to 4. That is, first of all, an ethanol extract from a raw material of propolis (see the Section <Isolation of Compounds>) was dissolved in 70% ethanol, and thereafter, standard agar media were prepared wherein the concentration of the extract was adjusted to be 0 ppm, 12.5 ppm, 25 ppm, 50 ppm, 100 ppm, or 150 ppm. Subsequently, these standard agar media were subjected to autoclave sterilization so as to prepare evaluation media, and each of the biological indicators was inoculated in each of these evaluation media so as to check out its growth and development. As a result, it has been confirmed that the higher the concentration of the ethanol extract is, the more strongly the growth and development of each of the biological indicators is inhibited. In particular, when the concentration of the ethanol extract is 30 ppm or more, or 50 ppm or more, no biological indicators were detected from the media. Incidentally, it was previously confirmed that 70% ethanol had almost no effect upon the growth and development of each of the biological indicators.

<Antimicrobial Activity Test with Compounds 1 to 4>

*E. coli* and *Salmonella enteritidis* (S. en; NBRC3313) as a biological indicator for Gram-negative bacteria; *Staphylococcus aureus* (Sta.) as a biological indicator for Gram-positive bacteria; and *Bacillus cereus* (B. ce) as a biological indicator for spore forming bacteria were used to evaluate the antimicrobial activity of each of Compounds 1 to 4. That is, first of all, each of Compounds 1 to 4 was dissolved in 70% ethanol, and thereafter, standard agar media were prepared wherein the concentration of each of Compounds 1 to 4 was adjusted to be 0 ppm, 5 ppm, 10 ppm, 15 ppm, 20 ppm, or 50 ppm. Subsequently, these standard agar media were subjected to autoclave sterilization so as to prepare evaluation media, and each of the biological indicators was inoculated in each of these evaluation media. After the incubation of each of the bacteria, the number of the bacteria per a petri dish (CFU/petri dish) was determined. The results are shown in Tables 3 and 4.

TABLE 3

| Concentration of Sample | | Number of Bacteria (CFU/petri dish) | | | |
|---|---|---|---|---|---|
| | | Gram-negative Bacteria | | Gram-positive Bacteria | Spore forming Bacteria |
| | | E. coli | S. en | Sta. | B. ce |
| 0 ppm | | >3000 | >3000 | 470 | 13 |
| Compound 1 | 5 ppm | >3000 | >3000 | 344 | 12 |
| | 10 ppm | >3000 | >3000 | 36 | 0 |
| | 15 ppm | >3000 | >3000 | 0 | 0 |
| | 20 ppm | >3000 | >3000 | 0 | 0 |
| | 50 ppm | >3000 | >3000 | 0 | 0 |
| Compound 2 | 5 ppm | >3000 | >3000 | 395 | 17 |
| | 10 ppm | >3000 | >3000 | 108 | 0 |
| | 15 ppm | >3000 | >3000 | 22 | 0 |
| | 20 ppm | >3000 | >3000 | 0 | 0 |
| | 50 ppm | >3000 | >3000 | 0 | 0 |

TABLE 4

| Concentration of Sample | | Number of Bacteria (CFU/petri dish) | | | |
|---|---|---|---|---|---|
| | | Gram-negative Bacteria | | Gram-positive Bacteria | Spore forming Bacteria |
| | | E. coli | S. en | Sta. | B. ce |
| 0 ppm | | 5 | 221 | 202 | 183 |
| Compound 3 | 5 ppm | 3 | 296 | 22 | 4 |
| | 10 ppm | 1 | 207 | 0 | 0 |
| | 15 ppm | 0 | 116 | 0 | 0 |
| | 20 ppm | 0 | 143 | 0 | 0 |
| | 50 ppm | 0 | 43 | 0 | 0 |
| Compound 4 | 5 ppm | 6 | 249 | 26 | 16 |
| | 10 ppm | 6 | 199 | 7 | 0 |
| | 15 ppm | 9 | 225 | 10 | 0 |
| | 20 ppm | 6 | 132 | 1 | 0 |
| | 50 ppm | 0 | 65 | 0 | 0 |

From the results as shown in Table 3, it has been found that the higher the concentration of Compound 1 or 2 is, the more strongly the growth and development of each of Gram-5 positive bacteria and spore forming bacteria is inhibited. Furthermore, it has been found that any of the concentrations of Compound 1 and any of the concentrations of Compound 2 have little effect upon the growth and development of each of *E. coli* and S. en. In addition, from this result it can be found that when Compound 1 or 2 as an antimicrobial ingredient is contained in a food and beverage product, a pharmaceutical, cosmetics or a quasi-drug, the concentration of Compound 1 or 2 in these products is preferably 10 ppm or more, and more preferably 15 ppm or more.

From the results as shown in Table 4, it has been found that each of Compounds 3 and 4 has an antimicrobial activity to any of the biological indicators, and in particular has a high antimicrobial activity to *E. coli*, Sta. and B. ce. Furthermore, from these results it can be also found that when Compound 3 as an antimicrobial ingredient is contained in a food and beverage product, a pharmaceutical, cosmetics or a quasi-drug, the concentration of Compound 3 in these products is preferably 10 ppm or more, and more preferably 15 ppm or more. Besides, from these results it can be also found that when Compound 4 as an antimicrobial ingredient is contained in a food and beverage product, a pharmaceutical, cosmetics or a quasi-drug, the concentration of Compound 4 in these products is preferably 10 ppm or more, and more preferably 50 ppm or more. Be noted that it was previously confirmed that 70% ethanol had little effect upon the growth and development of each of the biological indicators.

The invention claimed is:

1. An antioxidant comprising at least one substantially pure flavanone compound selected from nymphaeol-A, nymphaeol-B and nymphaeol-C.

2. An antimicrobial agent comprising at least one substantially pure flavanone compound selected from nymphaeol-A, nymphaeol-B and nymphaeol-C.

3. An antitumor agent comprising at least one substantially pure flavanone compound selected from nymphaeol-A, nymphaeol-B and nymphaeol-C.

4. A food and beverage product comprising at least one substantially pure flavanone compound selected from nymphaeol-A, nymphaeol-B and nymphaeol-C.

5. The food and beverage product according to claim 4, wherein the concentration of the flavanone compound contained in the food and beverage product is 30 ppm or more.

6. The food and beverage product according to claim 4, wherein the concentration of the flavanone compound contained in the food and beverage product is 30 ppm to 10,000 ppm.

7. A cosmetic comprising at least one substantially pure flavanone compound selected from nymphaeol-A, nymphaeol-B and nymphaeol-C.

8. A quasi-drug comprising at least one substantially pure flavanone compound selected from nymphaeol-A, nymphaeol-B and nymphaeol-C.

9. A pharmaceutical comprising at least one substantially pure flavanone compound selected from nymphaeol-A, nymphaeol-B and nymphaeol-C.

* * * * *